United States Patent [19]

Hanifin, Jr. et al.

[11] 4,170,656

[45] Oct. 9, 1979

[54] COMPOSITIONS CONTAINING CIS-2-BENZOYL-3-HYDROXY-CROTONONITRILE USED TO TREAT INFLAMMATION AND JOINT DETERIORATION

[75] Inventors: John W. Hanifin, Jr., Suffern; David N. Ridge, Upper Grandview, both of N.Y.

[73] Assignee: American Cyanamid Company, Stamford, Conn.

[21] Appl. No.: 892,002

[22] Filed: Mar. 31, 1978

Related U.S. Application Data

[63] Continuation-in-part of Ser. No. 801,899, May 31, 1977, abandoned.

[51] Int. Cl.$^2$ .............................. A61K 31/275
[52] U.S. Cl. ....................................... 424/304
[58] Field of Search ........................................ 424/304

[56] References Cited

PUBLICATIONS

Chem. Abst. 63—533b, (1965).

*Primary Examiner*—Stanley J. Friedman
*Attorney, Agent, or Firm*—Edward A. Conroy, Jr.

[57] ABSTRACT

This disclosure describes compositions of matter useful as anti-inflammatory agents and as inhibitors of the progressive joint deterioration characteristic of arthritic disease, and the methods of meliorating inflammation and of inhibiting joint deterioration in mammals therewith, the active ingredients of said composition of matter being certain cis-2-benzoyl-3-hydroxy-2-alkenonitriles and/or the pharmacologically acceptable cationic salts thereof.

3 Claims, No Drawings

COMPOSITIONS CONTAINING CIS-2-BENZOYL-3-HYDROXY-CROTONONITRILE USED TO TREAT INFLAMMATION AND JOINT DETERIORATION

CROSS REFERENCE TO RELATED APPLICATION

This application is a continuation-in-part of our co-pending application Ser. No. 801,899, filed May 31, 1977, now abandoned.

BRIEF SUMMARY OF THE INVENTION

This invention relates to novel compositions of matter useful as anti-inflammatory agents and as inhibitors of the progressive joint deterioration characteristic of arthritic disease. More particularly, it relates to therapeutic compositions containing certain cis-2-benzoyl-3-hydroxy-2-alkenonitriles or cationic salts thereof which meliorate inflammation and inhibit arthritic joint deterioration in mammals. The invention includes the new compositions of matter and the methods of meliorating inflammation and of inhibiting joint deterioration in mammals therewith. The active ingredients of the novel compositions of this invention may be represented by the following structural formula:

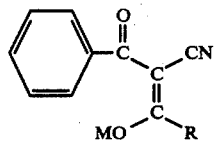

wherein R is alkyl having from one to four carbon atoms and M is hydrogen or a pharmaceutically acceptable cation. The useful pharmaceutically acceptable salts of the compounds of the above structural formula wherein M is hydrogen are those with pharmacologically acceptable metal cations, ammonium, amine cations or quaternary ammonium cations. Preferred metal cations are those derived from the alkali metals, e.g., lithium, sodium and potassium, and from the alkaline earth metals, e.g., magnesium and calcium, although cationic forms of other metals, e.g., aluminum, zinc, iron and in particular copper, are within the scope of the invention.

Pharmacologically acceptable amine cations and those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenylethylamine, ethylenediamine, diethylenetriamine, and aryliphatic amines containing up to and including 18 carbon atoms, as well as heterocyclic amines, e.g., piperidine, morpholine, pyrrolidine, piperazine and lower alkyl derivative thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxy-methyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The cis-2-benzoyl-3-hydroxy-2-alkenonitriles of the present invention may exist in other tautomeric forms as follows:

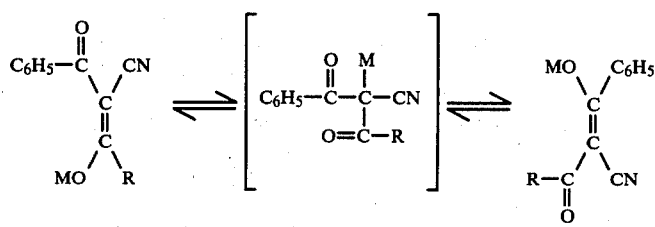

DETAILED DESCRIPTION OF THE INVENTION

The cis-2-benzoyl-3-hydroxy-2-alkenonitriles and cationic salts thereof of the present invention have been found to be highly useful for meliorating inflammation and inhibiting joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, topical or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned nonvolatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The cis-2-benzoyl-3-hydroxy-2-alkenonitriles are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following test shows the activity of the cis-2-benzoyl-3-hydroxy-2-alkenonitriles against chronic inflammation in adjuvant induced arthritis which is accompanied by joint destruction. Groups of three Royal Hart, Wistar strain rats weighing 200±10 grams each were injected intradermally in the right hind paw with Freund's adjuvant (dried human tubercle bacilli in a mineral oil vehicle) at a dose of 2 mg./kg. of body weight. Test compound was administered orally in a 1.5% starch vehicle at various doses once daily on days 0 through 13 post challenge. Control rats were treated in a similar manner, but given only starch vehicle. On the 14th and 21st day post challenge the diameter of the injected paw (primary lesion) was measured by micrometer caliper. The volume of inflamed paws were estimated from these measurements and the results are expressed as percent inhibition of swelling as compared to controls. At the same time, the other inflamed sites, such as ears, paws and tail (seconday lesions) were observed and each rat was graded as to degree of inflammation and swelling present. The grading is based on a scale of 0 to 24, where 0 represents a complete absence of induced arthritic nodules and 24 represents the maximum degree of inflammation. The mean grade for each treated group is calculated and the effects of each compound are expressed as percent inhibition of the control grade. Table I records the results of tests conducted with a typical compound of the present invention and known anti-inflammatory agents. The cis-2-benzoyl-3-hydroxycrotononitrile appears to suppress the progression of the arthritis and associated joint deterioration.

Table I

| | | | | | | % Inhibition | | % Inhibition of | |
| | Oral | | | | | of Swelling | | Control Grade | |
| | Dose | | | Mean Weight | | (primary lesion) | | (secondary lesion) | |
| | mg./kg. | | | Gain (grams) | | | | | |
| | of body | Dead/Treated | Day | Day | Day | Day | Day | Day |
| Compound | weight | At 21 Days | 14 | 21 | 14 | 21 | 14 | 21 |
|---|---|---|---|---|---|---|---|---|
| Normal Rats | — | 8/186 | 77 | 112 | — | — | — | — |
| Adjuvant Controls | — | 53/630 | 36 | 31 | 0 | 0 | 0 | 0 |
| Indomethacin | 2 | 8/57 | 68* | 68* | 51* | 24* | 38* | 25* |
| | 1 | 9/54 | 63* | 65* | 46* | 19* | 34* | 20* |
| | 0.5 | 5/54 | 53* | 51* | 40* | 20* | 25* | 17* |
| | 0.25 | 0/9 | 51 | 57* | 30* | 4 | 22* | 4 |
| Aspirin | 400 | 18/57 | 41 | 55* | 73* | 48* | 58* | 45* |
| | 200 | 10/66 | 40 | 44 | 48* | 27* | 26* | 17* |
| | 100 | 18/63 | 48 | 53* | 36* | 13 | 19* | 8 |
| | 50 | 2/21 | 56* | 44 | 23* | 3 | 12 | 9 |
| Phenylbuta- | 150 | 2/27 | 40 | 50* | 75* | 44* | 54* | 31* |

Table I-continued

The Effect of Anti-inflammatory Agents On Adjuvant Arthritis in Rats

| Compound | Oral Dose mg./kg. of body weight | Dead/Treated At 21 Days | Mean Weight Gain (grams) Day 14 | Day 21 | % Inhibition of Swelling (primary lesion) Day 14 | Day 21 | % Inhibition of Control Grade (secondary lesion) Day 14 | Day 21 |
|---|---|---|---|---|---|---|---|---|
| zone | 75 | 2/39 | 51* | 50* | 62* | 28* | 27* | 15 |
|  | 37.5 | 5/39 | 53* | 53* | 56* | 14 | 18 | 13 |
|  | 18.8 | 2/21 | 50* | 45 | 31 | 7 | 4 | 8 |
| Cis-2-benzoyl--3-hydroxy-crotononitrile | 100 | 5/18 | 43 | 41 | 68* | 53* | 38* | 46* |
|  | 50 | 3/36 | 51* | 45* | 64* | 54* | 14 | 17 |
|  | 25 | 3/18 | 37 | 28 | 26 | 14 | 10 | 1 |

*Significantly different from adjuvant controls.

Adjuvant induced experimental polyarthritis is a specific systemic disease of the rat which shares interesting similarities with rheumatoid arthritis. Specifically, the histology of the two diseases bears a remarkable resemblance as shown by C. M. Pearson et al., Am. J. Path. 42, 73 (1963). E. M. Glenn, Am. J. Vet. Res. 27 (116), 339 (1966) has classified adjuvant induced polyarthritis as a crippling and permanent deformity resulting from diffuse connective tissue involvement around certain susceptible joints in the rat. Zahiri et al., Can. Med. Ass. J. 101, 269 (1969) have shown that the fusiform swelling of the distal joints is associated with edema, congestion and synovitis including pannus formation, all of which precede the ultimate destruction of bone and cartilage. Furthermore, Zahiri et al. indicate that the cartilage destruction in the joint is due to an invasive pannus which originates in the marginal synovium and extends across the articular surface to erode it. When nonsteroidal, anti-inflammatory agents such as indomethacin inhibit arthritic paw swelling, which is composed of inflammatory cell infiltrates, they have also been shown to prevent joint and bone deterioration [see S. Wong et al., J. Pharm. & Exp. Ther. 185, 127 (1973) and G. R. Bobalick et al., Agents and Actions 4, 364 (1974)]. The most pertinent reference showing the relationship between arthritis and joint deterioration is an X-ray analysis of adjuvant arthritis in the rat by Blackham et al., Agents and Actions 7, 145 (1977). In a similar manner, inhibition of the progress of arthritis in paws of rats treated with the compounds of this invention also lessens associated joint deterioration.

Another method of determining a drug effect on conditions which result in inflammation is by measuring the effect on ultraviolet induced erythema in guinea pigs. Albino guinea pigs were depilitated on their flanks, the evening before testing, with a standard mixture of barium sulfide and gum acacia. On the morning of the test, groups of four guinea pigs were dosed by gavage one hour prior (−1 hour) to ultraviolet exposure. At 0 hour they were restrained in a plastic container which allows exposure of 3 circular spots. They were then exposed to ultraviolet irradiation from a "Hanovia" Kromayer lamp, model 10, for 60 seconds. At one and four hours, the degree of erythema for each of the three sites was assessed according to the following scoring system: 0=no erythema, 0.5=incomplete circle or faint erythema, and 1.0=complete circle of distinct erythema. Thus, the maximum score for each animal was 3.0. The following Table II summarizes the results of this test with a typical compound of the present invention and other drugs known to have a beneficial anti-inflammatory effect in suppressing ultra-violet induced erythema in warm blooded animals.

Table II

The Effect of Anti-inflammatory Agents on Development of Erythema in Guinea Pigs (pooled data)

| Oral Treatment | Dose mg./kg. of body weight | Score (avg.) 1 hour | 4 hours | Number | Decision |
|---|---|---|---|---|---|
| Control | — | 2.1 | 2.8 | 384 |  |
| Aspirin | 250 | 0.1 | 1.2 | 88 | A |
|  | 125 | 0.1 | 2.0 | 16 | A |
|  | 62.5 | 0.8 | 2.0 | 11 | A |
|  | 31.3 | 1.2 | 2.3 | 12 |  |
| Phenylbutazone | 250 | 0 | 0.5 | 60 | A |
|  | 125 | 0.1 | 1.1 | 16 | A |
|  | 62.5 | 0.3 | 0.9 | 12 | A |
|  | 31.3 | 0.4 | 17 | 12 | A |
|  | 15.6 | 0.4 | 2.3 | 8 | A |
|  | 7.8 | 1.1 | 2.9 | 8 |  |
| Indomethacin | 250 | 0 | 1.0 | 20 | A |
|  | 125 | 0 | 1.3 | 12 | A |
|  | 62.5 | 0 | 1.3 | 8 | A |
|  | 31.3 | 0.1 | 1.9 | 8 | A |
|  | 15.6 | 0 | 2.0 | 8 | A |
|  | 7.8 | 0.6 | 2.3 | 8 | A |
|  | 3.9 | 1.2 | 2.9 | 8 |  |
| Cis-2-benzoyl-3--hydroxy-crotononitrile | 125 | 0 | 1.3 | 8 | A |
|  | 62.5 | 0.8 | 2.4 | 4 | A |
|  | 31.3 | 0.8 | 2.3 | 4 | A |
|  | 15.6 | 2.3 | 2.5 | 4 |  |

A - Statistically significant activity - $p = < .05$ by t test

In determining the acute anti-inflammatory activity of the cis-2-benzoyl-3-hydroxy-2-alkenonitriles of the present invention, Royal Hart, Wistar strain rats, ranging in weight from 80 to 90 grams were used. The rats were fasted overnight prior to dosing but had free access to water. The test compounds were administered in aqueous suspension, by gavage, in a volume of 1.7 ml. per 50 grams of rat [corresponds to hydration volume used by Winter, et al., Proc. Soc. Exp. Biol. & Med., 111, 544–547 (1962)]. The phlogistic agent used was carrageenin prepared as a sterile 1% suspension in 0.9% aqueous sodium chloride for routine testing. A volume of 0.05 ml. was injected through a 26 gauge needle into the plantar tissue of the right hind paw. Measurements were made 5 hours after drug administration (4 hours after carrageenin challenge). Volumes of both the normal and carrageenin inflamed feet were determined. The difference between the two measurements is considered to be the increased edema due to the carrageenin administration. Results are expressed as a C/T efficacy ratio (edema of control animals/edema of treated animals) and a C/T ratio of greater than 1.41 is considered as active. Table III records the results of this test at the indicated dose level of a typical compound of the present invention and demonstrates the anti-inflammatory effect of this compound in comparison with known anti-inflammatory agents.

TABLE III

| Compound | Dose mg./kg. of Body Weight | No. of Rats | C/T Edema Ratio |
|---|---|---|---|
| Controls | — | 64 | — |
| Cis-2-benzoyl-3-hydroxy-crotonocitrile | 250 | 12 | 2.3* |
| Aspirin | 250 | 32 | 2.8* |
| Phenylbutazone | 250 | 32 | 2.3* |
| Indomethacin | 250 | 32 | 2.9* |

*Statistically significant activity p = < .05 by t test

This invention will be described in greater detail in conjunction with the following specific examples.

EXAMPLE 1

Benzoylacetonitrile, thallium (I) salt

A suspension of 10 g. of benzoylacetonitrile in 200 ml. of dry diethyl ether is stirred at room temperature while 17.2 g. of neat thallium (I) ethoxide is slowly added. The resulting reaction mixture is stirred for one hour at room temperature and then filtered. The collected precipitate is washed with diethyl ether and air dried whereby there is obtained 23.7 g. (99% yield) of the thallium (I) salt of benzoylacetonitrile which may be stored indefinitely at room temperature.

EXAMPLE 2

Cis-2-benzoyl-3-hydroxycrotononitrile

To a suspension of 2.2 g. of benzoylacetonitrile, thallium (I) salt in 20 ml. of tetrahydrofuran is added 2 ml. of acetyl fluoride with stirring at room temperature. After one hour, another 2 ml. of acetyl fluoride is added, followed by 2 ml. more after twelve hours. Twelve hours later, the precipitated thallium (I) fluoride is removed by filtration and the filtrate is evaporated to dryness. The off-white residue is recrystallized from ethanol to provide the cis-2-benzoyl-3-hydroxycrotononitrile which has been described by Musante, Gazz. Chim. Ital. 69, 523 (1939).

EXAMPLE 3

Cis-2-benzoyl-3-hydroxy-2-pentenonitrile

To a suspension of 5 g. of benzoylacetonitrile, thallium (I) salt in 50 ml. of diethyl ether is added a solution of 5 g. of propionyl fluoride in 10 ml. of diethyl ether with stirring at room temperature. After 12 hours, the reaction mixture is filtered and the filtrate evaporated and then pumped dry on a vacuum pump for one hour. The residue is then treated with chloroform and filtered and the solid collected provides the title compound.

EXAMPLE 4

Cis-2-benzoyl-3-hydroxy-2-hexenonitrile

The procedure of Example 2 is repeated substituting an equimolecular amount of butyryl fluoride for the acetyl fluoride employed in that example. There is thus obtained the cis-2-benzoyl-3-hydroxy-2-hexenonitrile after purification by column chromatography.

EXAMPLE 5

Cis-2-benzoyl-3-hydroxy-4-methyl-2-pentenonitrile

By replacing the acetyl fluoride employed in Example 2 with an equimolar amount of isobutyryl fluoride, there is obtained the corresponding cis-2-benzoyl-3-hydroxy-4-methyl-2-pentenonitrile after purification by column chromatography.

EXAMPLE 6

Cis-2-benzoyl-3-hydroxy-2-heptenonitrile

The general procedure of Example 2 is repeated but replacing the acetyl fluoride employed in that example with an equivalent amount of valeryl fluoride whereby there is obtained the cis-2-benzoyl-3-hydroxy-2-heptenonitrile after purification by column chromatography.

EXAMPLE 7

2-Methylbutyryl fluoride

A sample of 2-methylbutyryl chloride in dimethylformamide is treated with a threefold excess of sodium fluoride. The temperature is raised and the pure acid fluoride is collected by distillation from the reaction mixture.

EXAMPLE 8

Cis-2-benzoyl-3-hydroxy-4-methyl-2-hexenonitrile

Following the general procedure of Example 3, benzoylacetonitrile, thallium (I) salt is treated with 2-methylbutyryl fluoride to give the cis-2-benzoyl-3-hydroxy-4-methyl-2-hexenonitrile after purification by column chromatography.

EXAMPLE 9

Cis-2-benzoyl-3-hydroxy-5-methyl-2-hexenonitrile

Treatment of benzoylacetonitrile, thallium (I) salt with isovaleryl fluoride by the procedure described in Example 3 is productive of the cis-2-benzoyl-3-hydroxy-5-methyl-2-hexenonitrile after purification by column chromatography.

EXAMPLE 10

Cis-2-benzoyl-3-hydroxy-4,4-dimethyl-2-pentenonitrile

In the manner described in Example 3, reaction of benzoylacetonitrile, thallium (I) salt with pivalyl fluoride provides the corresponding cis-2-benzoyl-3-hydroxy-4,4-dimethyl-2-pentenonitrile after purification by column chromatography.

EXAMPLE 11

Cis-2-benzoyl-3-hydroxycrotononitrile, sodium salt

A calculated concentration of sodium hydroxide in water is prepared and an excess of cis-2-benzoyl-3-hydroxycrotononitrile is added and stirred for half an hour. The mixture is filtered and the filtrate is evaporated. The gummy residue is dissolved in dry acetone and again evaporated, providing the title compound.

EXAMPLE 12

Cis-2-benzoyl-3-hydroxy-2-pentenonitrile, triethylammonium salt

A sample of cis-2-benzoyl-3-hydroxy-2-pentenonitrile is dissolved in dry diethyl ether and an equivalent amount of triethylamine is added dropwise. The mixture is cooled in ice and the precipitate is removed by filtration to provide the title compound.

EXAMPLE 13

Cis-2-benzoyl-3-hydroxycrotononitrile, copper (II) salt

A weighed sample of cis-2-benzoyl-3-hydroxycrotononitrile is dissolved in a dilute solution of ammonium hydroxide and an equivalent quantity of cupric sulfate in water is added. The blue solution is heated on a steam bath for 3 hours and cooled. The precipitate is removed by filtration and washed with water to yield the title compound.

EXAMPLE 14

Preparation of 50 mg. Tablets

| Per Tablet | | Per 10,000 Tablets |
|---|---|---|
| 0.050 gm. | Cis-2-benzoyl-3-hydroxy-crotonitrile | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.0150 gm. | | 1490 gm. |

The cis-2-benzoyl-3-hydroxycrotononitrile, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 15

Preparation of Oral Suspension

| Ingredient | Amount |
|---|---|
| Cis-2-Benzoyl-3-hydroxy-2-pentenonitrile | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs ad | 100 ml. |

The sorbitol solution is added to 40 ml. of distilled water and the cis-2-benzoyl-3-hydroxy-2-pentenonitrile is suspended therein. The saccharin, sodium benzoate, flavor and dye are added and dissolved. The volume is adjusted to 100 ml. with distilled water. Each ml. of syrup contains 5 mg. of cis-2-benzoyl-3-hydroxy-2-pentenonitrile.

EXAMPLE 16

Preparation of Parenteral Solution

In a solution of 700 ml. of propylene glycol and 200 ml. of water for injection is suspended 20.0 grams of cis-2-benzoyl-3-hydroxy-2-hexenonitrile with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 17

Preparation of Topical Cream

| Ingredient | Amount |
|---|---|
| Cis-2-benzoyl-3-hydroxy-4-methyl-2-pentenonitrile | 1.0% |
| Ethoxylated stearyl alcohol | 10.0% |
| Benzyl alcohol | 0.9% |
| Isopropyl palmitate | 5.0% |
| Glycerin | 5.0% |
| Sorbitol solution (USP) | 5.0% |
| Lactic acid qs to pH 4.0-5.0 | |
| Water qs ad | 100.0% |

The ethoxylated stearyl alcohol and isopropyl palmitate are heated to liquifying temperature. About 95% of the total volume of water is placed in a separate container followed by the glycerin and sorbitol solution. This aqueous mixture is brought to a boil and then cooled to 60°-75° C. The cis-2-benzoyl-3-hydroxy-4-methyl-2-pentenonitrile is added to the wax phase and the mixture is stirred until a clear solution is obtained. The benzyl alcohol is added and dissolved in the wax phase. The water phase is passed through a screen into the wax phase while maintaining agitation. Both phases are kept at about the same temperature during transfer. The mixture is cooled while agitation is continued. At a temperature of 50°-55° C. the balance of the water is added. The pH is adjusted to 4.0-5.0 with lactic acid. The batch is cooled with minimum agitation until the cream sets in its final form.

EXAMPLE 18

Preparation of Intra-articular Product

| Ingredient | Amount |
|---|---|
| Cis-2-benzoyl-3-hydroxy-2-heptenonitrile | 2-20 mg. |
| NaCl (physiological saline) | 0.9% |
| Benzyl alcohol N.F. | 0.9% |
| Sodium carboxymethylcellulose | 1-5% |
| pH adjusted to 5.0-7.5 | |
| Water for injection qs ad | 100% |

EXAMPLE 19

Preparation of Injectable Depo Suspension

| Ingredient | % W/V |
|---|---|
| Cis-2-benzoyl-3-hydroxy-4,4-dimethyl-2-pentenonitrile | 0.05-5 |
| Polysorbate 80 USP | 0.2 |
| Polyethylene glycol 4000 USP | 3.0 |
| Sodium chloride USP | 0.8 |
| Benzyl alcohol N.F. | 0.9 |
| HCl to pH 6-8 | qs |
| Water for injection qs ad | 100.0 |

EXAMPLE 20

Cyanoacetone, sodium salt

A solution of 0.174 mole of sodium ethoxide is prepared by dissolving 4.0 g. of sodium in 200 ml. of absolute ethanol. A neat sample of 15 ml. (0.184 mole) of 5-methylisoxazole is then added dropwise as a colorless precipitate forms. When the addition is complete, the mixture is cooled in an ice bath and then filtered. The precipitate is collected, and washed with hexane, yielding 14.0 g. of colorless product.

EXAMPLE 21

Cis-2-benzoyl-3-hydroxycrotononitrile

A mixture of 1.0 g. (9.5 mmole) of cyanoacetone, sodium salt in 20 ml. of tetrahydrofuran is stirred at room temperature as a solution of 0.37 ml. (3.2 mmole) of benzoyl chloride in 5 ml. of tetrahydrofuran is added. The reaction is heated to reflux for 2 hours and the solvent is then evaporated. The residue is acidified and extracted with diethyl ether. Evaporation of the organic phase provides 0.7 g. of a yellow oil which crystallizes on standing to provide the title compound.

EXAMPLE 22

1-Cyano-2-butanone, sodium salt

A solution of 0.174 moles of sodium ethoxide is prepared by dissolving 4.0 g. of sodium in 200 ml. of absolute ethanol. A neat sample of 5-ethylisoxazole (17.9 g., 0.185 mole) is then added. The reaction is stirred for one hour as a colorless precipitate forms. The mixture is cooled in an ice bath and filtered. The precipitate is washed with hexane and air dried, yielding the title compound.

EXAMPLE 23

Cis-2-benzoyl-3-hydroxy-2-pentenonitrile

A mixture of 3.0 g. (25 mmole) of 1-cyano-2-butanone, sodium salt in 20 ml. of tetrahydrofuran is stirred as a solution of 0.9 g. (8.6 mmole) of benzoyl chloride in 6 ml. of tetrahydrofuran is added. The reaction is heated to reflux for 3 hours, then cooled and the solvent evaporated. The residue is acidified and extracted with chloroform. The organic phase is extracted twice with aqueous sodium bicarbonate which in turn is acidified and extracted again with chloroform. The organic phase is dried and evaporated to yield the title compound.

We claim:

1. The method of inhibiting the progression of arthritis in a mammal which comprises administering to said mammal an effective amount of a compound selected from the group consisting of those of the formula:

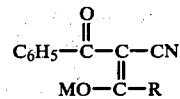

wherein R is an alkyl group having from one to four carbon atoms and M is hydrogen or a pharmacologically acceptable cation, and the tautomers thereof.

2. The method of inhibiting progressive joint deterioration in a mammal which comprises administering to said mammal an effective amount of a compound selected from the group consisting of those of the formula:

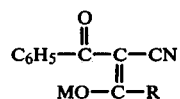

wherein R is an alkyl group having from one to four carbon atoms and M is hydrogen or a pharmacologically acceptable cation, and the tautomers thereof.

3. The method of meliorating inflammation in a mammal which comprises administering to said mammal an effective amount of a compound selected from the group consisting of those of the formula:

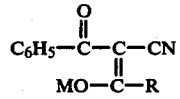

wherein R is an alkyl group having from one to four carbon atoms and M is hydrogen or a pharmacologically acceptable cation, and the tautomers thereof.

* * * * *